United States Patent [19]

Hidaka et al.

[11] 4,430,342
[45] Feb. 7, 1984

[54] N-ACYL-3-[4-(BENZOYLALKYL)PIPERAZIN-1-YL]-SYDNONIMINE COMPOUND, PROCESS FOR PRODCTION THEREOF, AND USE THEREOF

[75] Inventors: Hiroyoshi Hidaka, 799-75, Kannonji-cho, Tsu-shi, Mie-ken; Ikuo Matsumoto, Tokyo; Junji Yoshizawa, Machida; Shigenori Kotani, Kodaira, all of Japan

[73] Assignee: Hiroyoshi Hidaka, Mie, Japan

[21] Appl. No.: 420,873

[22] Filed: Sep. 21, 1982

[30] Foreign Application Priority Data

Oct. 6, 1981 [JP] Japan .................. 56-158100

[51] Int. Cl.³ .................. C07D 413/04; A61K 31/495
[52] U.S. Cl. ................................ 424/250; 544/367; 548/125
[58] Field of Search ................. 544/367; 424/250

[56] References Cited

U.S. PATENT DOCUMENTS

| | | | |
|---|---|---|---|
| 3,812,128 | 5/1974 | Masuda et al. | 544/367 |
| 3,833,580 | 9/1974 | Gotz et al. | 544/367 |
| 3,833,589 | 9/1974 | Simpson | 544/367 |

*Primary Examiner*—Donald G. Daus
*Assistant Examiner*—S. A. Gibson
*Attorney, Agent, or Firm*—Sherman & Shalloway

[57] ABSTRACT

An N-acyl-3-[4-(benzoylalkyl)piperazin-1-yl]-sydnonimine compound represented by the following formula

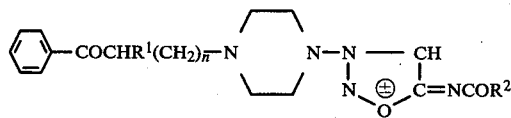

wherein
$R^1$ represents a hydrogen atom or an alkyl group having 1 to 8 carbon atoms,
$R^2$ represents a lower alkyl group, a lower alkoxy group or a phenyl group, and
n represents zero or an integer of 1 to 10, and its acid addition salt. The above sydnonimine compounds are useful for the treatment of troubles of the circulatory system and can be produced by contacting a 3-[4-(benzoylalkyl)-piperazin-1-yl]sydnonimine compound represented by the following formula

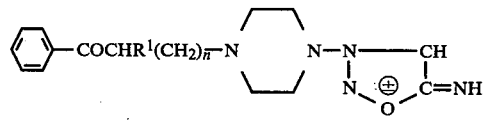

wherein $R^1$ and n are as defined, with a carboxylic acid represented by the following formula
$R^2COOH$ wherein $R^2$ is as defined.

8 Claims, No Drawings

N-ACYL-3-[4-(BENZOYLALKYL)PIPERAZIN-1-YL]-SYDNONIMINE COMPOUND, PROCESS FOR PRODCTION THEREOF, AND USE THEREOF

This invention relates to a novel sydnonimine derivative useful for the treatment of troubles of the circulatory system, a process for its production, and a pharmaceutical composition for the treatment of the aforesaid troubles.

More specifically, this invention relates to N-acyl-3-[4-(benzoylalkyl)piperazin-1-yl]sydnonimine compounds of the following general formula (1)

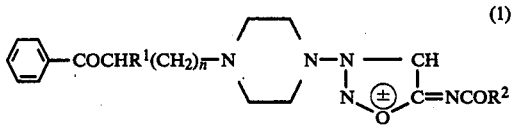

wherein $R^1$ represents a hydrogen atom or an alkyl group having 1 to 8 carbon atoms,
$R^2$ represents a lower-alkyl group, a lower alkoxy group or a phenyl group, and
n represents 0 or an integer of from 1 to 10,
and their acid addition salts. This invention also pertains to a process for the production of the compounds of formula (1) and their acid addition salts, and to a pharmaceutical composition comprising an amount, effective for the treatment of troubles of the circulatory system, of a compound of formula (1) or its acid addition salt and a pharmaceutically acceptable diluent or carrier.

Known derivatives of N-acyl-3-(piperazin-1-yl)-sydnonimines are those in which a lower alkyl, arylalkyl or aryl group is bonded to nitrogen at the 4-position of piperazine ring, and it is also known that these compounds are useful as medicines having unique pharmacological activities on the circulatory system and the central nervous system (Japanese Patent Publication No. 6265/1970).

We have been engaged in developing new piperazinosydnonimine derivatives, and finally succeeded in synthesizing the N-acyl-piperazinosydnonimine compounds having a benzoylalkyl group as represented by the above formula (1) and their acid addition salts which have not been described previously in the literature. We have also found that the compounds of formula (1) and their acid addition salts have coronary blood flow increasing activity, peripheral blood flow increasing activity, and platelet aggregation inhibiting activity, and are useful for the prevention and treatment of troubles of the circulatory system as peripheral circulation improvers, coronary artery dilators, cerebral thrombosis treating agents, etc.

It is an object of this invention therefore to provide novel N-acyl-piperazinosydnonimine compounds of formula (1) and their acid addition salts.

Another object of this invention is to provide a process for the production of the compounds of formula (1) and their acid addition salts.

Still another object of this invention is to provide a pharmaceutical composition comprising a compound of formula (1) or its pharmaceutically acceptable acid addition salt as an active ingredient.

The above and other objects and advantages of this invention will become more apparent from the following description.

In the compounds of this invention represented by formula (1), the $C_1$-$C_8$ alkyl group for $R^1$ may be a linear or branched alkyl group such as methyl, ethyl, propyl, isopropyl, butyl, sec-butyl, tert-butyl and pentyl. The lower alkyl group, preferably a $C_1$-$C_4$ alkyl group, for $R^2$ in formula (1), may be a linear or branched lower alkyl group such as methyl, ethyl, propyl, isopropyl and butyl, and the lower alkoxy group, preferably a $C_1$-$C_4$ alkoxy group, for $R^2$ may be a linear or branched lower alkoxy group such as methoxy, ethoxy, propoxy, isopropoxy, and tert-butoxy. In formula (1), n represents zero or an integer of from 1 to 10, preferably zero or an integer of from 1 to 7.

The acid addition salts of the compounds of formula (1) are preferably pharmaceutically acceptable acid addition salts. For example, they are salts with inorganic acids such as hydrochloric acid, nitric acid, sulfuric acid and phosphoric acid, and salts with organic acids such as formic acid, acetic acid, propionic acid, alkylsulfonic acids (e.g., methanesulfonic acid, ethanesulfonic acid and isothionic acid), arylsulfonic acids (e.g., benzenesulfonic acid and p-toluenesulfonic acids), oxalic acid, maleic acid and malic acid.

Examples of preferred compounds of formula (1) and their acid addition salts are as follows:
N-ethoxycarbonyl-3-[4-(4-benzoylbutyl)piperazin-1-yl)sydnonimine and its acid addition salts;
N-acetyl-3-[4-(benzoylmethyl)piperazin-1-yl]-sydnonimine and its acid addition salts;
N-benzoyl-3-[4-(benzoylmethyl)piperazin-1-yl]-sydnonimine and its acid addition salts;
N-ethoxycarbonyl-3-[4-(8-benzoyloctyl)piperazin-1-yl)sydnonimine and its acid addition salts;
N-benzoyl-3-[4-(4-benzoyl-6-methylheptyl)-piperazin-1-yl]sydnonimine and its acid addition salts; and
N-ethoxycarbonyl-3-[4-(benzoylmethyl)piperazin-1-yl]sydnonimine and its acid addition salts.

The compounds of formula (1) and their acid addition salts can be produced easily by contacting a 3-[4-(benzoylalkyl)piperazin-1-yl]sydnonimine compound represented by the following formula (2)

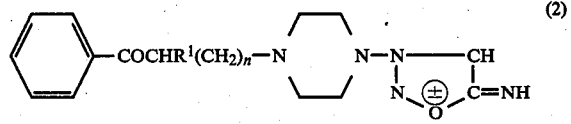

wherein $R^1$ represents a hydrogen atom or
an alkyl group having 1 to 8 carbon atoms,
and n represents zero or an integer of 1 to 10,
with a carboxylic acid represented by the following formula (3)

wherein $R^2$ represents a lower alkyl group,
a lower alkoxy group or a phenyl group,
or a reactive derivative thereof.

Examples of the reactive derivative of the carboxylic acid of formula (3) include halides, anhydrides and active esters of the carboxylic acids of formula (3). Illustrative of these reactive derivatives are anhydrides of the carboxylic acids of formula (3), halides, such as chlorides and bromides, of the carboxylic acids of formula (3), and active esters, such as 2,4-dinitrophenyl esters and phenyl thioesters, of the carboxylic acids of formula (3). When the carboxylic acid of formula (3) itself is used, it is preferred to carry out the reaction in the presence of a dehydrocondensing agent such as dicyclohexylcarbodiimide.

Since the condensing reaction between the compound of formula (2) and the compound of formula (3) is promoted in the presence of a tertiary amine, it is preferred to carry it out in pyridine or the like as a solvent. Other tertiary amines such as picoline, lutidine and triethylamine may also be used as the reaction solvent instead of pyridine. Or the reaction may be carried out in the presence of a catalytic amount of a tertiary amine in an aprotic solvent such as ether, dioxane, tetrahydrofuran and dimethylformamide.

The reaction temperature may be properly selected, and for example, temperatures of from about $-20°$ C. to about $60°$ C. are preferred. Usually, the reaction can be carried out at room temperature. The reaction time may also be properly selected. It may vary depending upon the reaction temperature, and is, for example, up to about 24 hours.

The desired compound of formula (1) may be obtained from the reaction mixture by, for example, diluting the reaction mixture with water and separating the precipitated compound of formula (1); or by evaporating the reaction solvent from the reaction mixture and extracting the residue with a solvent. The desired compound of formula (1) may be purified by known purifying means such as recrystallization and column chromatography.

An acid addition salt of the compound of formula (1) of this invention may be prepared by, for example, dissolving the compound of formula (1) in an alcoholic solvent, and adding about one equivalent of an acid. In this case, the acid addition salt is generally isolated as crystals.

The starting compound of formula (2) used in the process of this invention is also a novel compound not described in the literature, and can be produced, for example, by contacting a 4-(benzoylalkyl)-1-(N-nitrosocyanomethylamino)piperazine represented by the following formula (4)

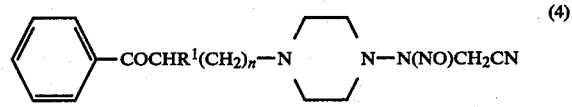

wherein $R^1$ and n are as defined, with an acid to induce cyclization reaction.

The compound of formula (4) can be easily produced, for example, by introducing a nitroso group into a 4-(benzoylalkyl)-1-(cyanomethylamino)piperazine of the following formula (5)

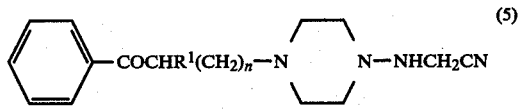

wherein $R^1$ and n are as defined with regard to formula (1).

The compound of formula (5) can be produced easily from a benzoylalkyl halide, for example. The synthetic route of the compound of formula (2) including steps of forming the staring compounds can be schematically shown as follows:

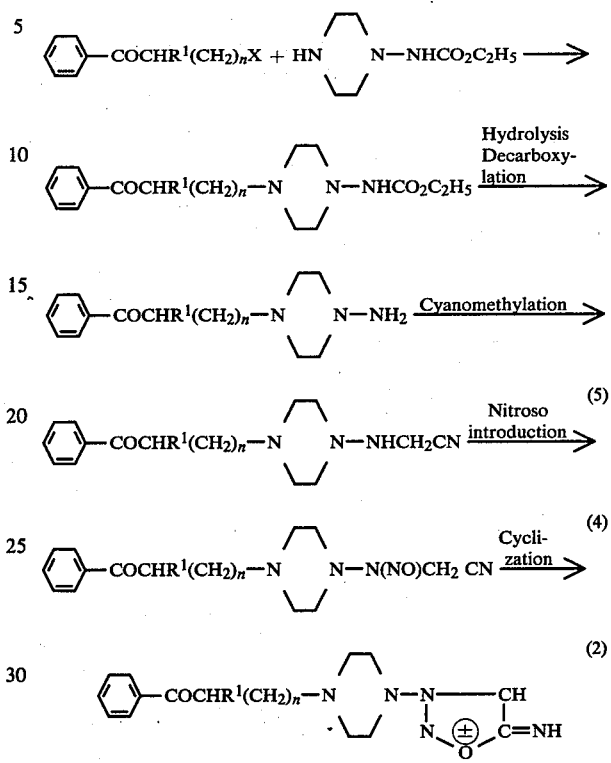

In the above formulae, X represents a halogen atom such as chlorine or bromine, and $R^1$ and n are as defined with regard to formula (1).

The compound of formula (5) can be produced, for example, by the following method.

A benzoylalkyl halide is reacted with 1-(ethoxycarbonylamino)piperazine in the presence of an excessive amount of an alkali bicarbonate to give a 4-(benzoylalkyl)-1-(ethoxycarbonylamino)piperazine. This reaction is carried out under heat in an alcohol solvent such as methanol, ethanol, isopropanol or butanol. The reaction product is isolated by solvent extraction. If desired, it may be purified by recrystallization. The resulting 4-(benzoylalkyl)-1-(ethoxycarbonylamino)piperazine is heated together with an alkali such as potassium hydroxide or sodium hydroxide, whereby hydrolysis and subsequently decarboxylation take place to yield a 4-(benzoylalkyl)-aminopiperazine. This hydrolysis and decarboxylation reaction is carried out in an alcohol solvent such as ethanol or methanol or a hydrous alcohol solvent such as hydrous ethanol or methanol at the boiling point of the solvent. The resulting 4-substituted-1-aminopiperazine can be isolated by solvent extraction. Usually, it is advantageous to use the reaction mixture directly in the subsequent step. The resulting 4-substituted-1-aminopiperazine solution is then neutralized by adding one equivalent of hydrochloric acid, and reacted first with formaldehyde sodium bisulfite hydrate and then with potassium cyanide to produce a cyanomethylaminopiperazine derivative. This cyanomethylation reaction may be carried out at a temperature of $50°$ to $70°$ C. The cyanomethylation product is isolated by extraction with an organic solvent, and if required, purified by recrystallization. The cyanomethylated derivative may be converted to its dihydrochloride by introducing hydrogen chloride into an ethanolic solution of it.

From the compound of formula (5) which can be obtained as above, the compound of formula (4) may be produced by introducing a nitroso group into the compound of formula (5) which can be obtained as shown above. This reaction can be carried out by utilizing known methods of nitrosozation. For example, it can be effected by reacting the dihydrochloride of the compound of formula (5) with an alkali nitrite such as sodium nitrite or potassium nitrite at a relatively low temperature. The reaction can be performed by contacting the dihydrochloride of the compound of formula (5) with the alkali nitrite in an aqueous medium at a relatively low temperature of, for example, about −5° C. to about 10° C. The reaction proceeds rapidly, and ends in 0.5 to 5 hours. The reaction product is isolated from the reaction mixture by solvent extraction. Without particularly purifying it, the product is used in the subsequent cyclization step. As required, however, it may be purified by recrystallization, etc.

By contacting the compound of formula (4) with an acid in the presence of a solvent, the compound of formula (2) is obtained in the form of its acid addition salt. Any inorganic or organic acid can be used in this cyclization reaction. Preferably, acids capable of forming pharmaceutically acceptable acid addition salts are used. Examples of preferred acids include such inorganic acids as hydrochloric acid, nitric acid, sulfuric acid and phosphoric acid and such organic acids as formic acid, acetic acid, propionic acid, alkylsulfonic acids (e.g., methanesulfonic acid, ethanesulfonic acid and isothionic acid), arylsulfonic acids (e.g., benzenesulfonic acid and p-toluenesulfonic acid), oxalic acid, maleic acid and malic acid.

Alcohols are preferred as the solvent used for the cyclization reaction, and lower alcohols such as methanol and ethanol may be cited as typical examples. The reaction is carried out preferably at relatively low temperature, for example about 0° C. to room temperature. Too high temperatures may result in undesirable side-reactions. The reaction time can be properly chosen, and may, for example, be about 5 to about 24 hours. The resulting acid addition salt may be isolated from the reaction mixture as a solid, and purified by recrystallization.

When the compound of formula (2) which can be obtained as above is used as a starting material for the compound of formula (1) of this invention, it may be used in the form of its acid addition salt.

The compounds of formula (1) of this invention show coronary blood flow increasing activity, but in an in vitro test, they do not show a relaxing activity on an extracted arterial vessel and an inhibitory activity on platelet aggregation. However, they do show an activity of increasing cerebral local blood flows in an in vivo test, and platelet aggregation inhibiting activity in an ex vivo test. The foregoing fact shows that the compounds of formula (1) are prodrugs which are activated upon undergoing metabolism in vivo. Furthermore, the compounds of formula (2) show a strong arterial vessel relaxing activity and a strong platelet aggregation inhibiting activity in in vitro tests. It is presumed from this fact that the active metabolite of the compound of formula (1) of this invention will be the 3-[4-(benzoylalkyl)piperazin-1-yl]sydnonimine of formula (2).

Table 1 summarizes the results of in vitro tests in which the human platelet aggregation inyibitory activity of the 3-[4-(benzoylalkyl)piperazin-1-yl]sydnonimines of formula (2) and their relaxing activity on the extracted mesenteric artery of a rabbit were examined.

The mesenteric artery relaxing activity is shown by the conversion ($\mu$M) of a drug required to induce 50% of the maximum relaxation, and the platelet aggregation inhibiting activity, by the concentration ($\mu$M) of a drug required to inhibit collagen-induced platelet aggregation to an extent of 50%.

TABLE 1

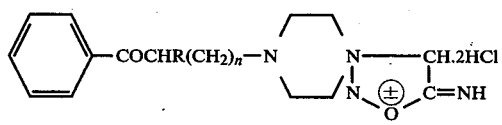

| R | n | Mesenteric artery relaxing activity ($\mu$M) | Platelet aggregation inhibiting activity ($\mu$M) |
|---|---|---|---|
| H | 0 | 0.16 | 0.14 |
| H | 2 | 2.3 | 5.4 |
| H | 3 | 0.2 | 3.4 |
| H | 4 | 3.0 | 6.3 |
| H | 5 | 0.12 | 0.94 |
| H | 7 | 0.058 | 0.028 |
| iso-C$_4$H$_9$ | 3 | 1.3 | 11.0 |

For example, in a test for inhibition of platelet aggregation using a rabbit, the activity of the compound of formula (1) lasts longer than the activity of the compound of formula (2), and this shows the compound of formula (1) to have an excellent property as a medicine.

Pharmacological tests on N-carboethoxy-3-[4-(4-benzoylbutyl)piperazin-1-yl]sydnonimine (compound A), a typical example of the compound of formula (1) of this invention, are shown below.

Pharmacological tests (1) Activity on the extracted heart

The increase or decrease of the coronary blood flow was examined by the Langendorf's method using the extracted heart of a guinea pig. When 0.1 ml of the compound A ($10^{-4}$ g/ml solution) was injected, a 14% increase was observed in the coronary blood flow. On the other hand, when 0.1 ml of morsydmine ($10^{-4}$ g/ml solution) was injected, no increase in the coronary blood flow was observed.

(2) Activity on the local cerebral blood flow (a) Activity on the hippocampus and amygdaloid nucleus (by the hydrogen gas clearance method) Rabbits having a body weight of about 3 kg, five per group, were used. A tracheal cannula was inserted into each rabbit under sodium pentobarbital anesthesia, and under artificial respiration, gallamine triethiodide was intravenously administered in a dose of 2 mg/kg to immobilize it. The animal was then fixed to a brain stereotaxic apparatus (Todai Noken type). Gallamine triethiodide was also intramuscularly administered in a dose of 3 mg/kg every one hour.

The local cerebral blood flow was measured by the hydrogen gas clearance method (UH meter, PHG-201, manufactured by Unique Medical Co., Ltd.). Platinum electrodes having a diameter of 300 $\mu$m and coated with an epoxy resin were inserted in the hippocampus (P:4, L:5, H:+5) and the amygdaloid nucleus (A:2, L:6, H:−6) in accordance with the brain atlas of Sawyer et al. An indifferent electrode was placed under the skin of the head and fixed there. After a waiting time of more than 30 minutes until the blood flow was stabilized, about 8% hydrogen gas was caused to be inhaled for three minutes through a side tube of the tracheal cannula, and a clearance curve was drawn. The resulting curve was plotted semilogarithmically, and the half-time period (T ½) was determined by the initial slope method. The blood flow was calculated from the following equation.

Blood flow F=69.3/T ½(ml/min./100 g)

The blood flow was measured every thirty minutes. When the blood flow became constant, the test drug or the control drug was intravenously administered, and the measurement was made until 1 hour after the administration. The change in the blood flow was expressed by the percent change based on the blood flow before the administration of the drug. When the compound A (0.5 mg/kg) was administered as the test drug, an increase of 5 to 15% was observed at the hippocampus and an increase of about 10%, at the amygdaloid nucleus. When the morsydmine (0.5 mg/kg) as a control drug was administered, an increase of 10 to 20% was observed at the hippocampus and an increase of about 15%, at the amygdaloid nucleus. Thus, the compound A has as strong an activity on the blood flow of the hippocampus and the amigdaloid nucleus as the morsydmine.

(b) Activity on the cerebral cortex (a cross thermocouple method)

Male rabbits having a body weight of about 3 kg, five per group, were used. Under sodium pentobarbital anesthesia, a tracheal cannula was inserted into each rabbits, and under artificial respiration, 2 mg of gallamine triethiodide was intravenously injected to immobilize the animals. The animals were each fixed to a brain stereotaxic apparatus (Todai Noken type). An element of the double needle type (WN-301, manufactured by Unique Medical Co.) was inserted into the frontal contex through a hole provided by a dental drill, and variations in potential were recorded. After the blood flow was stabilized, the test drug and a control drug were each administered through a cannula inserted into the retro-auricular vein of the right ear. The percent increase in the blood flow was calculated by taking the blood flow at death as 0 and the blood flow before drug administration as 100%. When the compound A (0.5 mg/kg) was administered as the test drug, the blood flow increased by 10 to 20%. But when the control drug, morsydmine, (0.5 mg/kg) was administered, no increase in the blood flow was noted.

(3) Platelet aggregation inhibiting action

Rabbits having a body weight of about 3 kg, three per group, were used. In a group, the compound A was administered intravenously in a dose of 5 mg/kg to one rabbit; 3-[4-(4-benzoylbutyl)piperazin-1-yl]sydnonimine dihydrochloride (compound A') was administered to another rabbit intravenously in a dose of 5 mg/kg; and the remaining one rabbit was used as a control. The blood was drawn from each of the rabbits periodically. Citric acid was added to each of the blood samples, and the mixture was centrifuged to separate the plasma.

A solution containing 10 μM of ADP (adenosine diphosphate) was added to 0.4 ml of each of the plasma samples, and the induced platelet aggregation was measured by using an aggregometer. By a similar method, platelet aggregation induced by collagen (an extract of the bovine tendon) was measured.

The results of the test were expressed by the percent inhibition of platelet aggregation determined by taking the percent inhibition for the control animal as 0.

TABLE 2

| Compound | Platelet aggregation inhibiting agent | Time after administration (minutes) | | | | |
|---|---|---|---|---|---|---|
| | | 5 | 30 | 60 | 180 | 300 |
| Compound A | ADP | 16 | 99 | 96 | 87 | 37 |
| | Collagen | 29 | 98 | 100 | 91 | 61 |
| Compound A' | ADP | 97 | 100 | 33 | 9 | 0 |
| | Collagen | 95 | 99 | 59 | 5 | 0 |

Thus, according to this invention, there can be provided a pharmaceutical composition comprising an amount, effective for treating troubles of the circulatory system, of an N-acyl-3-[4-(benzoylalkyl)piperazin-1-yl]sydnonimine compound of the following formula (1)

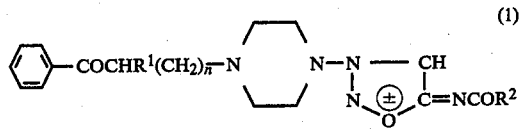

wherein R¹ represents a hydrogen atom or an alkyl group having 1 to 8 carbon atoms,
R² represents a lower alkyl group, a lower alkoxy group or a phenyl group and
n represents zero or an integer of from 1 to 10,
or its pharmaceutically acceptable acid addition salt, as a prodrug, and a pharmaceutically acceptable diluent or carrier.

The pharmaceutical composition of this invention may be in various forms prepared by methods known in the pharmaceutical field. For example, it may be in the form of powders, granules, tablets, injections, capsules, etc. The pharmaceutically acceptable diluent or carrier used in the pharmaceutical composition of this invention may be any liquid or solid diluent or carrier known in pharmaceutical fields. Examples of such a liquid or solid diluent or carrier include distilled water, ethanol, isopropanol, propylene glycol, glycerol, lactose, corn starch, crystalline cellulose, talc, stearic acid, magnesium stearate, carboxymethyl cellulose, hydroxypropyl cellulose, gum arabic and beeswax.

The pharmaceutical composition of this invention may contain the compound of formula (1) in any amount which is effective for the treatment of troubles of the circulatory system. For example, its amount is 0.01 to 99% by weight based on the weight of the pharmaceutical composition. The dose of the compound of formula (1) in accordance with this invention may, for example, be about 0.1 to about 100 mg/body/day, preferably about 0.3 to about 30 mg/body/day. The toxicity of the compounds (1) of this invention is extremely low as shown by the results of a test described hereinbelow.

Preferred examples of the compounds of formula (1) are those in which R¹ is a hydrogen atom or an isobutyl group, and their acid addition salts. Compounds of formula (1) in which n is 0, 2, 3, 4, 5 or 7 and their acid addition salts are also preferred. The especially preferred compound is N-carboethoxy-3-[4-(4-benzoyl-butyl)piperazin-1-yl]sydnonimine.

The acute toxicity of the in vivo active type of this typical compound as a prodrug was tested by using male dd-strain mice (body weight 16 to 20 g). It was found that the $LD_{50}$ of the present compound A was 91 mg/kg in intravenous administration, 350 mg/kg in subcutaneous administration, and 750 mg/kg in oral administration.

The following examples illustrate the present invention specifically.

REFERENTIAL EXAMPLE 1

4-(4-Benzoylbutyl)-1-(ethoxycarbonylamino)-piperazine:

29.2 g of 5-bromovalerophenone and 23 g of 1-(ethoxycarbonylamino)piperazine were dissolved in 250 ml of ethanol. 30.5 g of sodium hydrogen carbonate was added, and the mixture was heated under reflux for 6 hours. Ethanol was evaporated from the reaction mixture. After addition of water, the residue was extracted with benzene. The extract was recrystallized from benzene-hexane to give 36.2 g of the title compound having a melting point of 105° to 106° C.

4-(4-Benzoylbutyl)-1-aminopiperazine:

30.0 g of 4-(4-benzoylbutyl)-1-(ethoxycarbonylamino)piperazine was dissolved in 250 ml of ethanol, and a solution of 50.5 g of potassium hydroxide in 50 ml of water was added. The mixture was heated under reflux for 3 hours. Ethanol was evaporated, and water was added. Extraction with chloroform gave 27.0 g of the title compound. The hydrochloride of this product had a melting point of 213° to 215° C. (decomp.).

4-(4-Benzoylbutyl)-1-(cyanomethylamino)piperazine dihydrochloride:

33.2 g of 4-(4-benzoylbutyl)-1-aminopiperazine was dissolved in 300 ml of 50% hydrous ethanol, and 19 g of sodium hydroxymethanesulfonate monohydrate was added. They were reacted at 55° to 60° C. for 2 hours. Under reduced pressure, ethanol was removed, and 150 ml of water was added. Then, a solution of 10.8 g of potassium cyanide in 100 ml of water was added, and the reaction was carried out at 55° to 60° C. for 3 hours. The reaction mixture was extracted with ether, and the extract was dissolved in ethanol. On addition of ethanolic hydrochloric acid, 33.3 g of the title compound having a melting point of 177° to 178° C. (decomp.) was obtained.

3-[4-(4-benzoylbutyl)piperazin-1-yl]sydnonimine dihydrochloride:

5.0 g of 4-(4-benzoylbutyl)-1-(cyanomethylamino)-piperazine dihydrochloride was dissolved in 50 ml of water, and under ice cooling, a solution of 2.0 g of sodium nitrite in 20 ml of water was added dropwise. The reaction was carried out for 1 hour. The reaction mixture was extracted with chloroform. Chloroform was evaporated, and the residue was dissolved in 30 ml of methanol. Then, 30 ml of 12% ethanolic hydrochloric acid was added, and the reaction was carried out for two days at room temperature. The precipitated crystals were collected by filtration to give 3.7 g of the title compound having a melting point of 168° C. (decomp.).

REFERENTIAL EXAMPLE 2

When a benzoylalkyl halide as a starting material was treated in the same way as in Referential Example 1, 3-[4-(benzoylalkyl)piperazin-1-yl]sydnonimine dihydrochlorides shown in the following table were obtained.

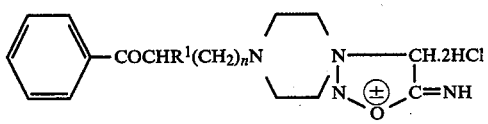

| R¹ | n | Melting point (°C.) |
|---|---|---|
| H | 0 | 182–184 (decomp.) |
| H | 2 | 176 (decomp.) |
| H | 4 | 173 (decomp.) |
| H | 5 | 164–165 (decomp.) |
| H | 7 | 160–162 (decomp.) |
| iso-$C_4H_9$ | 3 | 165 (decomp.) |

EXAMPLE 1

50 ml of pyridine was added to 9.5 g of 3[4-(4-benzoylbutyl)piperazin-1-yl]sydnonimine dihydrochloride, and with ice cooling and stirring, 11 ml of ethyl chloroformate was added. The mixture was stirred at room temperature for 3 hours. The reaction mixture was poured into ice water, and the precipitate was crystallized from ethanol to give 8.6 g of N-ethoxycarbonyl-3-[4-(4-benzoylbutyl)piperazin-1-yl]sydnonimine having a melting point of 151° C. (decomp.).

Elemental analysis (%) for $C_{20}H_{27}N_5O_4$:

| | C | H | N |
|---|---|---|---|
| Calculated | 59.84 | 6.78 | 17.44 |
| Found | 59.55 | 6.69 | 17.45 |

IR, $\nu_{max}^{KBr}$ (cm$^{-1}$): 3140, 3040, 2950, 2930, 2890, 2850, 2820, 2770, 1680, 1660, 1600, 1590, 1480, 1460, 1440, 1425, 1410, 1385, 1360, 1350, 1330, 1320, 1280, 1260, 1205, 1170, 1140, 1120, 1070, 1055.

UV, $\lambda_{max}^{H2O}$ (nm): 233 ($\epsilon=21,150$), 317 ($\epsilon=14,000$).

NMR (CDCl$_3$, 60 Mz) $\delta$ppm: 1.28 (t, J=7.0 Hz, 3H), 1.4–2.0 (m, 4H), 2.47 (t, J=6.8 Hz, 2H), 2.99 (t, J=6.2 Hz, 2H), 2.68 (t, J=4.7 Hz, 4H), 3.48 (t, J=4.7 Hz, 4H), 4.12 (q, J=7.0 Hz, 2H), 7.3–7.6 (m, 3H), 7.62 (s, 1H), 7.8–8.0 (m, 2H).

EXAMPLE 2

3 ml of pyridine was added to 0.54 g of 3-[4-(benzoylmethyl)piperazin-1-yl]sydnonimine dihydrochloride, and 0.6 ml of acetic anhydride was added under ice cooling. Then, the mixture was stirred at room temperature for 2 hours. The reaction mixture was poured into ice water, and the precipitate was recrystallized from ethanol to give 0.40 g of N-acetyl-3-[4-(benzoylmethyl)-piperazin-1-yl]-sydnonimine having a melting point of 162° to 164° C. (decomp.).

IR, $\nu_{max}^{KBr}$ (cm$^{-1}$): 3130, 3050, 2950, 2880, 2800, 1680, 1610, 1590, 1540, 1450, 1400, 1390, 1375, 1355, 1340, 1300, 1270, 1220, 1200, 1180, 1150, 1105·1050.

NMR (DMSO-d$_6$) $\delta$ppm: 1.98 (s, 3H), 2.7–3.0 (m. 4H), 3.4–3.7 (m. 4H), 4.98 (s, 2H), 7.3–7.7 (m, 3H), 7.8–8.1 (m, 2H), 8.23 (s, 1H).

EXAMPLE 3

The same reaction as in Example 2 was carried out except that 0.35 ml of benzoyl chloride was used instead of acetic anhydride. Recrystallization of the product from methanol gave 0.45 g of N-benzoyl-3-[4-benzoylmethyl)piperazin-1-yl]sydnonimine having a melting point of 140° to 142° C. (decomp.).

IR, $\nu_{max}^{KBr}$ (cm$^{-1}$): 3180, 3100, 3050, 2950, 2900, 2800, 1685, 1620, 1580, 1560, 1480, 1420, 1400, 1390, 1370, 1355, 1340, 1325, 1310, 1290, 1270, 1220, 1185, 1175, 1150, 1120, 1060.

NMR (DMSO-d$_6$, 60 Mz) δppm: 2.7–3.0 (m, 4H) 3.5–3.8 (m, 4H), 4.99 (s, 2H), 7.3–7.7 (m, 6H), 7.8–8.2 (m, 4H), 8.51 (s, 1H).

EXAMPLE 4

The same reaction as in Example 2 was carried out except that 0.72 ml of ethyl chloroformate was used instead of acetic anhydride. Recrystallization of the product from methylene chloride-methanol gave 0.48 g of N-ethoxycarbonyl-3-[4-(benzoylmethyl)piperazin-1-yl]sydnonimine having a decomposition point of 185° to 186° C. (decomp.).

Elemental analysis for $C_{17}H_{21}N_5O_4$ (%):

|  | C | H | N |
|---|---|---|---|
| Calculated | 56.82 | 5.89 | 19.49 |
| Found | 56.67 | 5.93 | 19.31 |

IR, $\nu_{max}^{KBr}$ (cm$^{-1}$): 3150, 3000, 2955, 2900, 2800, 1700, 1660, 1655, 1570, 1460, 1420, 1400, 1385, 1370, 1350, 1310, 1295, 1275, 1230, 1220, 1195, 1160, 1135, 1125, 1085.

UV, $\lambda_{max}^{MeOH}$ (nm): 233 (ε=22,000), 317 (ε=14,800).

NMR (CDCl, 60 Mz) δppm: 1.27 (t, J=7.0 Hz, 3H), 2,8–3.1 (m, 4H), 3.4–3.7 (m, 4H), 390 (s, 2H), 4.12 (q, J=7.0 Hz, 2H), 7.2–7.6 (m, 3H), 7.61 (s, 1H), 7.8–8.0 (m, 2H).

EXAMPLE 5

3 ml of pyridine was added to 0.50 g of 3-[4-(8-benzoyloctyl)piperazin-1-yl]sydnonimine dihydrochloride, and with ice cooling and stirring, 0.5 ml of ethyl chloroformate was added. The mixture was stirred at room temperature for 3 hours. The reaction mixture was poured into ice water, and the precipitate was recrystallized from ethanol to give 0.36 g of N-ethoxycarbonyl-3-[4-(8-benzoyloctyl)piperazin-1-yl]sydnonimine having a melting point of 136° to 137° C. (decomp.).

IR, $\nu_{max}^{KBr}$ (cm$^{-1}$): 3150, 3040, 2920, 2850, 1675, 1655, 1600, 1595, 1490, 1470, 1450, 1420, 1405, 1370, 1360, 1340, 1310, 1295, 1270, 1230, 1215, 1200, 1160, 1120, 1070, 1040.

NMR (CDCl, 60 Mz) δppm: 1.1–2.0 (m, 15H), 2.1–2.6 (m, 2H), 2.68 (t, J=4.5 Hz, 4H), 2.94 (t, J=7.0 Hz, 2H), 3.50 (t, 4.5 Hz, 4H), 4.13 (q, J=7.0 Hz, 2H), 7.2–7.6 (m, 3H), 7.63 (s, 1H), 7.8–8.1 (m, 2H).

EXAMPLE 6

3 ml of pyridine was added to 0.50 g of 3-[4-(benzoyl-6-methylheptyl)piperazin-1-yl]sydnonimine dihydrochloride, and with ice cooling and stirring, 0.25 ml of benzoyl chloride was added. The mixture was stirred at room temperature for 3 hours. The reaction mixture was poured into ice water, and the precipitate was recrystallized from hydrous ethanol to give 0.44 g of N-benzoyl-3-[4-(4-benzoyl-6-methylheptyl)piperazin-1-yl]sydnonimine having a melting point of 100° to 102° C.

IR, $\nu_{max}^{KBr}$ (cm$^{-1}$): 3140, 3040, 2930, 2850, 2780, 1660, 1620, 1580, 1540, 1460, 1440, 1415, 1405, 1385, 1355, 1320, 1290, 1270, 1235, 1210, 1130, 1110, 1060.

NMR (CDCl$_3$, 60 Mz) δppm: 0.88 (d, J=3.4 Hz, 6H), 1.1–1.9 (m, 7H), 2.0–2.3 (m, 1H), 2.31 (t, J=6.2 Hz, 2H), 2.56 (t, J=4.8 Hz, 4H), 3.44 (t, J=4.8 Hz, 4H), 7.2–7.6 (m, 6H), 7.7–8.4 (m, 5H).

EXAMPLE 7

400 mg of N-ethoxycarbonyl-3-[4-(4-benzoylbutyl)-piperazin-1-yl]sydnonimine obtained in Example 1 was dissolved in 5 ml of methanol, and 130 mg of oxalic acid dihydrate was added to give an oxalate salt of the abovementioned sydnonimine.

When hydrochloric acid, nitric acid and maleic acid were individually used instead of oxalic acid, the corresponding salts were obtained.

The recrystallization solvents for these salts and the melting points and water solubilities of the salts are summarized in the following table.

|  | Recrystallizing solvent | Melting point (°C.) | Solubility in water (%) |
|---|---|---|---|
| Oxalate | Methanol | 152 (decomp.) | 0.46 |
| Maleate | Methanol/ether | 128 (decomp.) | 0.94 |
| Hydrochloride | Methanol/ether | 151 (decomp.) | 0.89 |
| Nitrate | Methanol | 118 (decomp.) | 0.43 |

EXAMPLE 8

The solubility of the N-ethoxycarbonyl-3-[4-(4-benzoylbutyl)piperazin-1-yl]sydnonimine obtained in Example 1 in water dilute hydrochloric acid and the Carmody's buffer was measured by the absorbance of the solution at 317 nm.

Solubility in water at 25° C.: 0.001%

Solubility in dilute hydrochloric acid at 25° C.:

| Normality | 0.001 (pH 3) | 0.01 (pH 2) | 0.1 (pH 1) |
|---|---|---|---|
| Solubility (%) | 0.23 | 0.63 | 1.04 |

Solubility in Carmody's buffer at 25° C.:

| pH | 7 | 6 | 5 | 4 | 3 | 2 |
|---|---|---|---|---|---|---|
| Solubility (%) | 0.01 | 0.04 | 0.10 | 0.44 | 0.93 | 1.56 |

What is claimed is:

1. An N-acyl-3-[4-(benzoylalkyl)piperazin-1-yl]-sydnonimine compound represented by the following formula

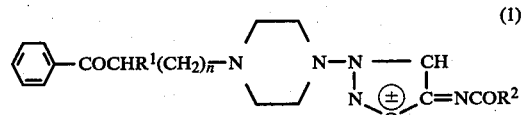

wherein R$^1$ represents a hydrogen atom or an alkyl group having 1 to 8 carbon atoms, R$^2$ represents a lower alkyl group, a lower alkoxy group or a phenyl group, and n represents zero or an integer of 1 to 10, and its acid addition salt.

2. N-ethoxycarbonyl-3-[4-(4-benzoylbutyl)piperazin-1-yl]sydnonimine and its acid addition salt according to claim 1.

3. N-acetyl-3-[4-(benzoylmethyl)piperazin-1-yl]-sydnonimine and its acid addition salt according to claim 1.

4. N-benzoyl-3-[4-(benzoylmethyl)piperazin-1-yl]-sydnonimine and its acid addition salt according to claim 1.

5. N-ethoxycarbonyl-3-[4-(8-benzoyloctyl)piperazin-1-yl]sydnonimine and its acid addition salt according to claim 1.

6. N-benzoyl-3-[4-(4-benzoyl-6-methylheptyl)-piperazin-1-yl]sydnonimine and its acid addition salt according to claim 1.

7. N-ethoxycarbonyl-3-[4-(benzoylmethyl)piperazin-1-yl]sydnonimine and its acid addition salt according to claim 1.

8. A pharmaceutical composition comprising an amount, effective for treating troubles of the circulatory system, of an N-acyl-3-[4-(benzoylalkyl)piperazin-1-yl]-sydnonimine compound represented by the following formula (1)

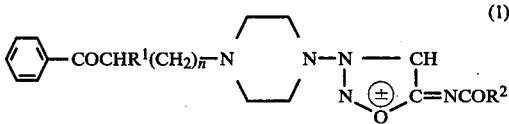

wherein $R^1$ represents a hydrogen atom or an alkyl group having 1 to 8 carbon atoms, $R^2$ represents a lower alkyl group, a lower alkoxy group or a phenyl group, and n represents zero or an integer of 1 to 10, or its pharmaceutically acceptable acid addition salt and a pharmaceutically acceptable diluent or carrier.

* * * * *